United States Patent [19]

Dyke

[11] 4,304,869
[45] Dec. 8, 1981

[54] APPARATUS FOR RUPTURING A SEALED, FRANGIBLE CONTAINER

[75] Inventor: Denis G. Dyke, Edinboro, Pa.

[73] Assignee: American Sterilizer Company, Erie, Pa.

[21] Appl. No.: 153,136

[22] Filed: May 27, 1980

[51] Int. Cl.³ .............................................. C12M 1/24
[52] U.S. Cl. ................................... 435/296; 206/219; 206/222; 215/227; 215/DIG. 8; 435/299; 435/300; 435/810; 435/31
[58] Field of Search ............... 206/219, 222; 215/227, 215/DIG. 8; 435/287, 296, 299, 300, 301, 292, 293, 294, 295, 317, 810, 801, 31

[56] References Cited

U.S. PATENT DOCUMENTS

| | | | |
|---|---|---|---|
| 1,774,258 | 8/1930 | English | 206/222 |
| 2,275,567 | 3/1942 | Smith | 215/DIG. 8 |
| 2,619,448 | 11/1952 | Larsen | 206/219 X |
| 3,440,144 | 4/1969 | Andersen | 435/31 |
| 3,451,894 | 6/1969 | Anandam | 435/801 X |
| 3,638,918 | 2/1972 | Denholtz | 206/222 |
| 3,655,035 | 4/1972 | Mühlbauer | 206/219 |
| 3,661,717 | 5/1972 | Nelson | 435/31 |
| 3,739,947 | 6/1973 | Baumann et al. | 206/219 X |
| 3,762,540 | 10/1973 | Baumann et al. | 206/219 |

FOREIGN PATENT DOCUMENTS 1144883  10/1957  France .............................. 206/219

Primary Examiner—Robert J. Warden
Attorney, Agent, or Firm—Robert D. Yeager

[57] ABSTRACT

Apparatus for rupturing a sealed, frangible container is disclosed. A substantially rigid tubular member, closable at both ends if desired, is provided with a zone of reduced interior cross section. The tubular member is adapted to receive the frangible container and retain it in a position so that an annular space of decreasing dimension is formed adjacent the zone of reduced cross section of the tubular member. Means insertable into the annular space wedgedly engage the frangible container with sufficient force to rupture it.

18 Claims, 8 Drawing Figures

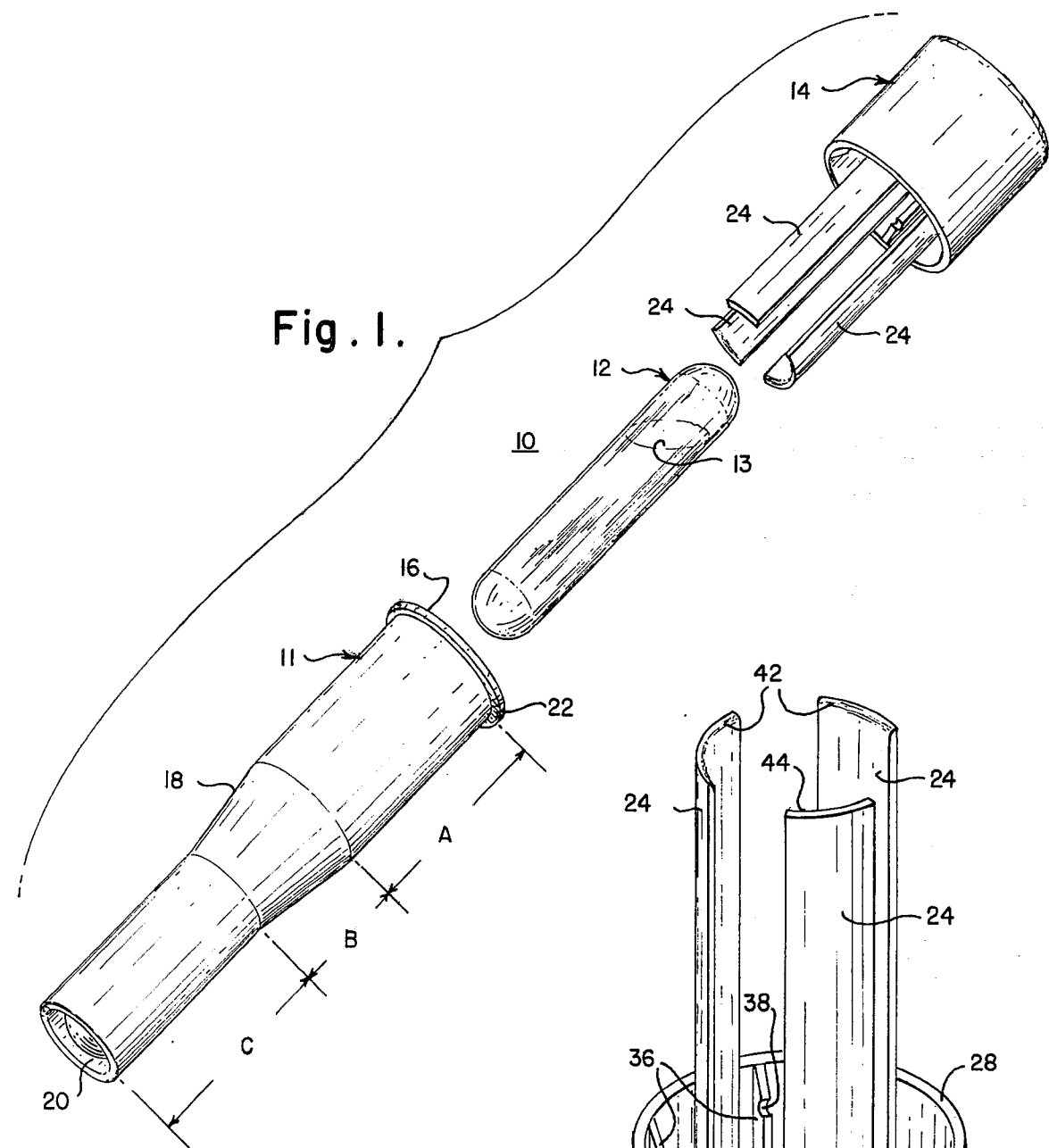

APPARATUS FOR RUPTURING A SEALED, FRANGIBLE CONTAINER

BACKGROUND OF THE INVENTION

1. Field of the Invention

This invention relates to apparatus for rupturing a sealed, frangible container such as a glass ampul.

2. Description of the Prior Art

Hermetically sealed glass ampuls are widely used, particularly in the health care industry, for containing fluids that must be protected against contact by external influences at least until the contained fluids are ready for use. Such ampuls find application, for example, in hypodermic injection apparatus and with biological indicating systems. In the latter, it is generally desirable to provide immediate and massive contact of the fluid contained in the ampul with external influences; in such case, rupturing the ampul by some means has been the preferred technique as contrasted with a puncturing technique that might be used with hypodermic injection apparatus. Such immediate and massive outflow of contained fluid from an ampul also might be desirable where the fluid is to be applied as a measured quantity to some other apparatus or is to flood a zone or substance.

The conventional technique for rupturing an ampul involves encasing the ampul in a flexible tube or sleeve and, by the use of the operator's fingers, crushing or breaking the ampul; see U.S. Pat. Nos. 3,661,717 and 3,440,144. While effective to provide the desired immediate outflow of the contents of the ampul, this technique poses the risk of injury to the operator and/or the possibility of contamination and error, by the potential for glass chards penetrating the protective covering over the ampul.

SUMMARY OF THE INVENTION

The present invention overcomes the disadvantages inherent in conventional apparatus for rupturing a sealed, frangible container, such as an ampul, by the use of a substantially rigid tubular member, in which the container is retained, coacting with means insertable into the tube for wedgedly engaging the container with sufficient force to rupture it. The wedging action between the tubular member and the frangible container may be provided in a variety of ways, but most conveniently is provided by adjusting the surface contours of the inside of the tube to define an annular space of decreasing dimension between tube and container into which space the insertable means is thrust. The radially compressive forces on the container walls generated by this wedging action increase until the container fractures.

The present invention thereby provides apparatus for rupturing a sealed, frangible container comprising: a substantially rigid tubular member having a zone of reduced interior cross section along its longitudinal axis and being dimensioned to receive the container with at least a portion thereof extending into the zone of reduced interior cross section to define thereat an annular space; means disposed within the tubular member for retaining the container in a position that preserves the defined annular space; and means insertable into the annular space for wedgedly engaging a portion of the frangible container with sufficient force to rupture it. Preferably, the portion of the tubular member having a reduced cross section is tapered and the annular space is of decreasing dimension in the direction of the taper. Also preferably, the wedgedly engaging means includes a plurality of elongated, flexible, spaced arms having surface portions configured to conform with the surfaces of the interior of the tubular member and the container.

The means in the present invention for retaining the container in position within the tubular member may comprise means for closing one end of the tubular member, means supported by the interior walls of the tubular member, or some other suitable means. The tubular member also may be closed at its opposite end by closure means which is operatively connected to the wedgedly engaging means. In this latter embodiment, the application of the closure to the tubular member serves to thrust the wedgedly engaging means into the annular space between the tube and container to rupture the container.

The foregoing and other features and advantages of the present invention will be more completely disclosed in the following detailed description, the accompanying drawings and the appended claims.

BRIEF DESCRIPTION OF THE DRAWINGS

FIG. 1 is an exploded assembly view, in perspective, of one embodiment of the present invention;

FIG. 2 is an enlarged isometric view, with portions broken away for clarity, of a closure means for use in the present invention;

DETAILED DESCRIPTION OF THE PREFERRED EMBODIMENTS

Figure 4:
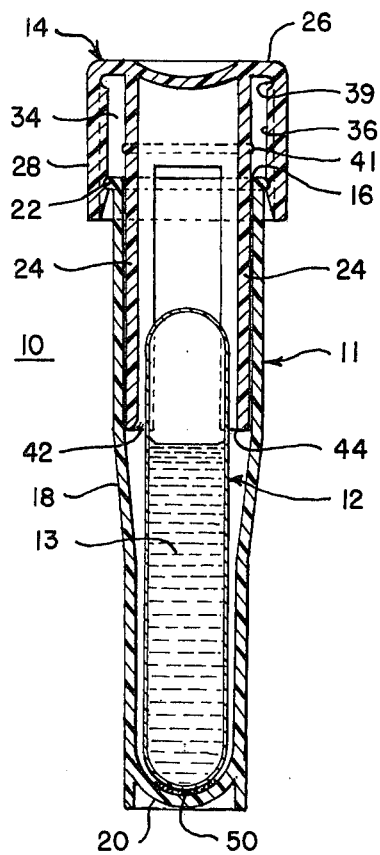
FIG. 4 is a vertical section of the embodiment of the present invention illustrated in FIGS. 1-3, taken generally on the plane indicated in FIG. 3 and developed, showing the closure means in a first position.

The apparatus of the present invention finds particularly useful application as a biological indicator for sterilization processes. Before proceeding with a description of an embodiment of the invention in that context, a brief explanation of the use of such indicators will be helpful.

To test the effectiveness of a steam or gas sterilization process, standardized spores of a strain sufficiently resistant to the sterilization medium are placed on a carrier (such as a spore strip) and are exposed to the sterilization process being tested. Sterilization of the standardized spore strain insures sterilization of bacterial strains in the chamber load; survival of the standardized spore strain indicates unsatisfactory sterilization of the load.

Survival of the spores subsequent to the sterilization process is determined by mixing a test solution consisting of growth medium and a pH indicator with the spores and incubating the culture for growth. In spore fermentation, for example, glucose contained in the growth medium is utilized by viable spores and pyruvic acid is produced as a by-product. Pyruvic acid lowers the pH of the test solution and thus causes a change of color of the pH indicator in the solution. If, however, there are no viable spores following sterilization, the pH (and thus the color) of the test solution remains essentially unchanged.

Referring then to the drawings, particularly to FIGS. 1–5, an embodiment of the present invention in a biological indicator 10 of unitary structure will now be described. Biological indicator 10 includes a tubular vial 11 closed at one end, a sealed ampul 12 adapted to be received within vial 11 and containing an appropriate test solution 13, and a complementary closure 14 for the open end of vial 11. The cooperation of these components, as described in detail below, provides a mechanism for rupturing ampul 12 to release its contents 13 to the environment of the interior of vial 11.

Vial 11 comprises an elongated,, tapered tube having its largest diameter at the open end 16 and tapering through a necked-down section 18 to a smaller diameter at closed end 20. Vial 11 is made of a substantially rigid, clear material such as polycarbonate. For use in a biological indicator, vial 11 may be dimensioned as follows: The wall thickness is 0.035 inches. Open end 16 has a flanged circumferential portion 22 having an outside diameter of 0.552 inches and an inside diameter of 0.435 inches. A first tapered portion A extends a distance of 0.830 inches from flanged portion 22. A second and critically tapered portion B begins with an inside diameter of 0.420 inches and extends for 0.42 inches to an inside diameter of 0.343 inches. The latter inside diameter is maintained along portion C of vial 11 to a point 1.850 inches from flanged portion 22; curved portion 20 having a radius of 0.167 inches closes the end of vial 11.

Ampul 12 is of conventional cylindrical design with spherical closed end portions and is constructed of frangible glass. In the present embodiment, ampul 12 is 1.75 inches in length and has a uniform diameter of 0.315 inches±0.079 inches.

Closure (or cap) 14 is constructed to snugly fit over open end 16 of vial 11 and, in cooperation with flanged portion 22, to provide two degrees of closure of vial 11. By means of projections 24 extending from the interior portion of cap 14, means are provided to rupture ampul 12 in a manner soon to be described.

Cap 14 preferably is constructed of a semi-rigid material such as polypropylene and may be of any suitable color since visibility is not essential to cap 14. Cap 14 includes a circular top portion 26 and a cylindrical outer wall 28. Molded into top 26 is an inner cylindrical wall 30, radially spaced from and of substantially less height than outer wall 28. An annulus 34 thereby is formed between outer and inner walls 28 and 30. Extending downwardly from inner wall 30 is at least one projection 24. In the embodiment shown in the drawings, three such projections 24, uniformly spaced about the circumference of inner wall 30 and each rounded across its width, are shown. The purpose of projections 24, when moved longitudinally into vial 11 as hereinafter described, is to provide a wedging action between vial 11 and ampul 12 and a resultant compressive force on ampul 12 sufficient to crush it.

Figure 3:
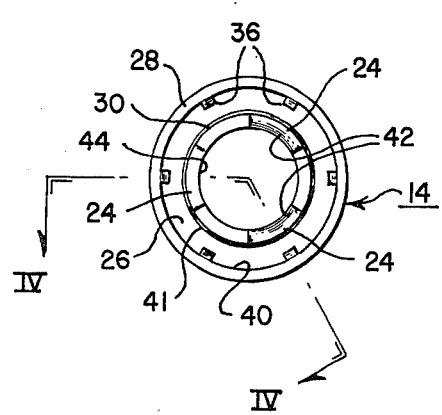
FIG. 3 is a plan view of the closure means of FIG. 2.

As best shown in FIGS. 2 and 3, the inner surface of outer wall 28 of cap 14 has a series of spaced, longitudinally extending ribs 36 formed thereon. Ribs 36 each have inwardly extending first notches 38 equidistantly spaced from the open end of cap 14 to receive flanged portion 22 of vial 11 and thereby provide a first locking position for cap 14 on vial 11. Ribs 36 terminate short of the inside surface of top 26 with inwardly extending second notches 39 to permit flanged portion 22, upon further sliding movement of cap 14 over vial 11 beyond the first locking position just described, to lock firmly against the junction 40 of outer wall 28 and top 26. The locking engagement of flanged portion 22 of vial 11 in notches 39 of cap 14 is referred to herein as the second locking position of cap 14 on vial 11. The longitudinal distance between the first and second locking positions is about 0.312 inches. A circumferential sealing bead 41 is molded onto the outer surface of inner wall 30 to engage the inner surface of vial 11 when cap 14 is in the second locking position and thereby seal the interior of vial 11 from contact with extraneous external elements.

In typical dimensions when cap 14 is used in a biological indicating device, the wall thickness generally is ~0.040 inches, the inside diameter of outer wall 28 is 0.578 inches, inner wall 30 has an outside diameter of 0.434 inches and a height of about 0.3 inches, and the cap has an overall height of 0.50 inches. The three projections 24 descend from inner wall 30 of cap 14 a distance of about 0.93 inches and each has an outer chord width of 0.210 inches. The inside diameter of inner wall 30 and the effective inside diameter of projections 24 throughout their length is 0.325 inches.

While a single projection 24, in coaction with the inner walls of vial 11 and ampul 12, will be sufficient to cause the rupture of ampul 12, it is preferred to provide a plurality of projections 24. For example, a closure 14 constructed with three projections 24 as shown in the drawings provides a centering action as the closure is moved longitudinally with respect to vial 11. Wider molding tolerances also are enjoyed with a plurality of projections. The multiple projections also serve to cradle an ampul carried in vial 11 during handling and shipping.

As best shown in FIG. 2, projections 24 are constructed to apply forces unequally to the walls of ampul 12 to minimize the force necessary to move closure 14 from its first locking position to its second locking position and thus to rupture ampul 12. This imbalance in the distribution of forces is accomplished by providing two of the projections with rounded inner edges 42 and the third with a squared edge 44. As projections 24 move longitudinally between the walls of vial 11 and ampul 12, the rounded edges 42 tend to glide smoothly along ampul 12 while the squared edge 44 serves to concentrate the compressive forces exerted inwardly against ampul 12.

Figure 5:
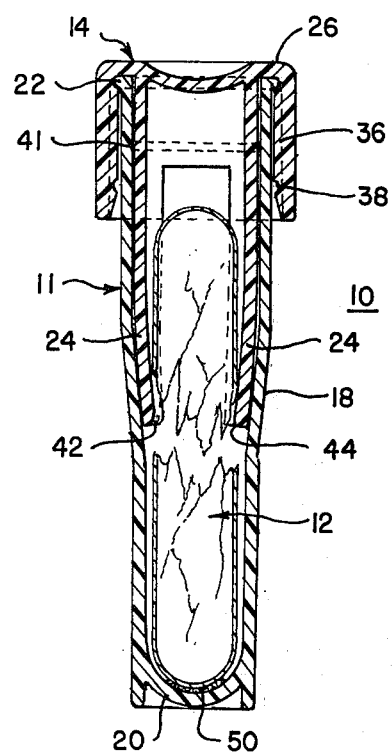
FIG. 5 is a vertical section similar to FIG. 4, also taken generally on the plane indicated in FIG. 3 and developed, showing the closure means in a second position.

The operation of the present invention in biological indicator 10 will now be described by particular reference to FIGS. 4 and 5. In FIG. 4 there is shown ampul 12 disposed within vial 11. Ampul 12 contains a test solution 13 consisting of nutrient media, such as trypticase soy broth, and a pH chemical indicator, such as phenol red; phenol red is an alkaline indicator which changes color to yellow upon contact with acid. A biological spore disc 50 of a suitable standardized strain, such as *Bacillus subtilis* (used in ethylene oxide sterilization) or *Bacillus stearothermophilus* (used in steam sterilization), is placed at the base of vial 11. Alternatively, spore disc 50 may be positioned within vial 11 at necked-down section 18 so that there is more immediate contact between the disc and the contents of ampul 12 when it is shattered at that point. Ampul 12 is supported at the bottom of vial 11 either by spore disc 50 resting on rounded bottom 20 or by rounded bottom 20 itself.

Closure 14 is placed over the open end 16 of vial 11 and is moved longitudinally with respect thereto to the first locking position. In this position, the ends of projections 24 are located at the approximate point where critical tapered section B of vial 11 begins and are not in substantial contact with ampul 12.

Biological indicator device 10 arranged as shown in FIG. 4 then is placed into a sterilization chamber. With cap 14 in its first locking position, gaseous sterilant is free to enter vial 11 by passing through the annular space between flanged portion 22 of vial 11 and the inner surface of outer wall 28 of cap 14. Accordingly, spore disc 50 is exposed to sterilization, but the tortuous path provided in cap 14 for the entry of gaseous sterilant tends to prevent entry into vial 11 of extraneous orgnisms in the sterilizer atmosphere.

After completion of the sterilization cycle, biological indicator device 10 is removed from the sterilization chamber. The operator applies pressure on the top of cap 14 in a longitudinal direction to move cap 14 out of its first locking position and into its second locking position (see FIG. 5). This movement causes projections 24 to flex inwardly and move downwardly into the annulus about ampul 12 in tapered section B of vial 11. Continued movement of projections 24 into the narrowing annulus within that section results in a wedging action and the build-up of radially inward compressive forces on ampul 12. As the movement of the ends of projections 24 proceeds toward the longitudinal midpoint of ampul 12, its most vulnerable area to compressive forces, the walls of frangible ampul 12 finally give way and the ampul ruptures, releasing its contents 13 into vial 11 for contact with spore disc 50. At the same time, vial 11 is sealed with cap 14 in its second locking position by the engagement of bead 41 with the inner walls of vial 11 and subsequent contamination of the interior of vial 11 by airborne bacteria is prevented.

The contents of vial 11 are incubated for a period of generally seven days to observe for growth and fermentation of viable bacteria. If viable bacterial spores are present, they will ferment glucose in the nutrient media to produce pyruvic acid, thereby lowering the pH of the solution and causing the phenol red to change from red to yellow. Such a color change indicates a positive test result (growth) and an unsatisfactory sterilization process. When the solution remains red, a negative test result (no growth) is obtained and thus a satisfactory sterilization process is assured.

Figure 6:
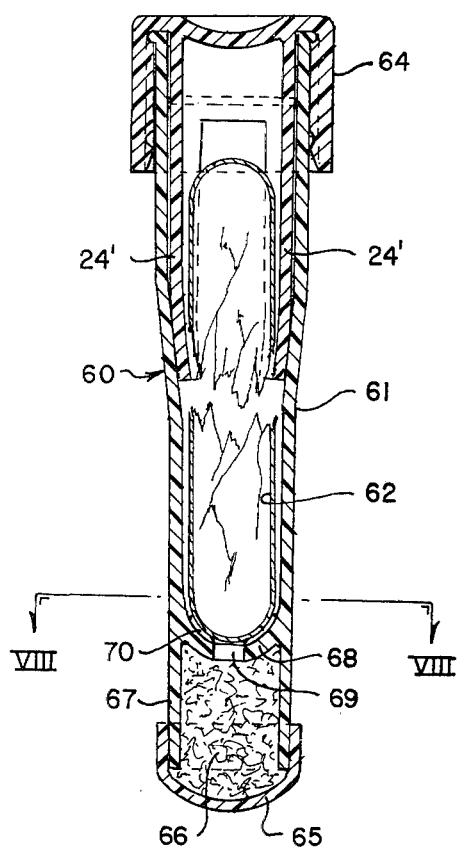
FIG. 6 is a vertical section of a further embodiment of the present invention, similar to the showing of FIG. 5, which embodiment is a fluid applicator device.
Figure 8:
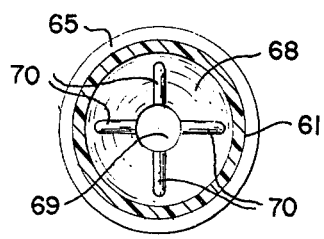
FIG. 8 is a sectional view, taken along the line VIII—VIII of FIG. 6.

The present invention also may find advantageous use in an applicator. For example, iodine is an unstable liquid that tends to decompose upon contact with air. If iodine could be carried in a sealed ampul which could be ruptured to charge an applicator just prior to use, the problem of iodine decomposition could be avoided or minimized. FIGS. 6 and 8 may be referred to in the following description of the present invention in an applicator.

Applicator 60 includes a tubular vial 61 open at both ends, a sealed ampul 62 adapted to be received within vial 11 and containing a liquid, say iodine, to be applied, and complementary closures 64 and 65 for the open ends of vial 61. The cooperation of these components, as described hereinafter, provides a mechanism for rupturing ampul 62 to release the iodine into a cotton swab 66 packed into a compartment within vial 61 located below ampul 62. When swab 66 is saturated, cap 65 may be removed and applicator 60 is ready for use.

Vial 61, ampul 62 and cap 64 are constructed identically to vial 11, ampul 12 and cap 14 described above except for structure now to be described that provides a housing for cotton swab 66 and permits the flow of iodine into that swab after ampul 62 is ruptured. Compared with the showing of FIG. 4, vial 61 includes cylindrical wall portion 67 extending below rounded bottom 68 (20 in FIG. 4) to provide a compartment into which cotton swab 66 is packed. Rounded bottom 68 includes a central opening 69 to permit the flow of liquid from ampul 62 into that compartment. In order to prevent the rounded bottom portion of ampul 62 from acting as a check valve in opening 69 of rounded bottom 68, upstanding spaced ribs 70 are molded on the upper side of rounded bottom 68 to support ampul 62 in spaced relation from bottom 68. A snugly fitting cap 65, formed of rubber or other flexible material, is provided for the open end of cylindrical wall portion 67.

In the applicator embodiment of the present invention shown in FIG. 6, the rupturing of ampul 62 is effected in the same manner as described above in the biological indicator embodiment. Although cap 64 is shown in FIG. 6 as a two position cap identical to cap 14 described above, that feature is not essential to the operation of the applicator embodiment. All that is necessary is to provide projections 24' depending from cap 64 to provide the wedging engagement action described above for rupturing ampul 62.

Figure 7:
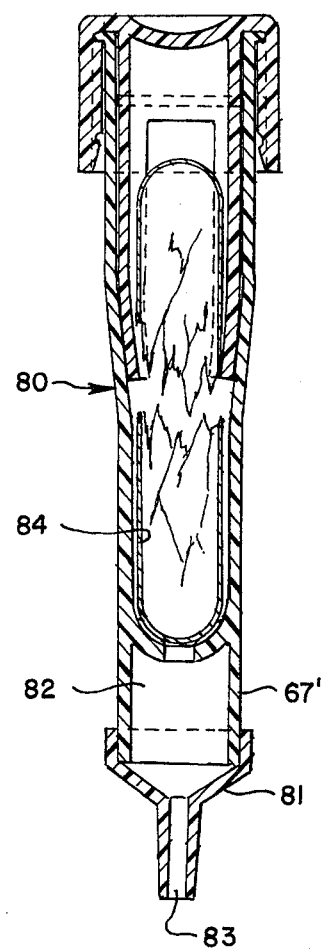
FIG. 7 is a vertical section of a still further embodiment of the present invention, also similar to the showing of FIG. 5, which embodiment is a fluid feeding device.

Still further, the present invention may be embodied in a device for supplying a measured quantity of fluid to some other apparatus. This further embodiment is illustrated in FIGS. 7 and 8. Referring to FIG. 7, device 80 is identical to applicator 60 except that cap 65 is replaced by a funnel member 81 which may be cemented onto the end of cylindrical wall portion 67'. The compartment 82 formed by cylindrical wall portion 67' is not filled with cotton material, but may contain a filtering substance to prevent the passage of any glass chard through the outlet 83 of funnel member 81.

In operation, outlet 83 of funnel member 81 is inserted into an appropriate port of the apparatus (not shown) into which the contents of ampul 84 are to be discharged. Ampul 84 is ruptured in the same manner as described in connection with applicator 60. The contents of ampul 84 flow out of outlet 83 either by gravity or by the application of a pressure differential.

What is claimed is:

1. Apparatus for rupturing a sealed, frangible container comprising:
   a substantially rigid tubular member having a zone of reduced interior cross section along its longitudinal axis and being dimensioned to receive said container with at least a portion thereof extending into said zone of reduced interior cross section to define thereat an annular space;
   means disposed within said tubular member for retaining said container in a position that preserves said defined annular space; and
   flexible means insertable into said annular space for wedgedly engaging a portion of said frangible container with sufficient force to rupture it.

2. Apparatus as recited in claim 1 wherein:

said zone reduced cross section is tapered and said annular space is of decreasing dimension in the direction of said taper.

3. Apparatus as recited in claim 2 wherein:
said flexible wedgedly engaging means comprises a plurality of elongated, spaced arms having surface portions configured to conform with the surfaces of the interior of said tubular member and said container.

4. Apparatus as recited in claim 3 wherein:
at least one of said arms has formed at the end adapted for applying force to said frangible container an edge portion and the corresponding ends of the remaining arms have rounded portions.

5. Apparatus as recited in claim 1 wherein:
said container retaining means comprises means for closing one end of said tubular member.

6. Apparatus as recited in claim 5 that further comprises:
closure means for the opposite end of said tubular member, said closure means being operatively connected to said wedgedly engaging means.

7. Apparatus as recited in claim 6 wherein said closure means for said opposite end of said tubular member includes:
means for releasably engaging said opposite end of said tubular member in a first position wherein the interior of said tubular member is in communication with the outside atmosphere; and
means for sealingly engaging said opposite end of said tubular member in a second position.

8. Apparatus as recited in claim 1 wherein:
said container retaining means comprises means supported by the interior walls of said tubular member for engaging said container.

9. Apparatus as recited in claim 1 wherein:
said tubular member includes a transverse wall having an opening therein and said container retaining means is supported by said transverse wall.

10. Apparatus as recited in claim 9 wherein:
said container retaining means includes a plurality of spaced projections from said transverse wall.

11. Apparatus for use in a biological indicator comprising:
a substantially rigid, transparent, closable, tubular member having a zone of reduced interior cross section along its longitudinal axis;
a sealed, frangible container disposed within said tubular member, and being positionable therein to permit a portion of said container to extend into said zone of reduced cross section to define an annular space; and
flexible means insertable into said annular space for wedgedly engaging a portion of said frangible container with sufficient force to rupture it.

12. Apparatus as recited in claim 11 wherein:
said frangible container carries a solution comprising a growth medium for spores and a pH indicator; and
spores carried by a substrate are disposed within said tubular member.

13. Apparatus as recited in claim 11 wherein:
said tubular member is closed at one end, said closed end serving to support said container in a position that perserves said defined annular space.

14. Apparatus as recited in claim 13 which further comprises:
closure means for the opposite end of said tubular member, said closure means being operatively connected to said wedgedly engaging means.

15. Apparatus for use in a biological testing system comprising:
a substantially rigid, transparent, tubular member adapted for closure at both ends and having a zone of tapered interior cross section along its longitudinal axis;
a cap adapted to engage the end of said tubular member opposite the direction of said taper and being moveable on said end between a first position, wherein the interior of said tubular member is in communication with the outside atmosphere, and a second position, wherein said cap sealingly engages said end;
a frangible, sealed container co-axially disposed within said tubular member; and
a plurality of flexible projections depending from said cap and constructed to wedge between said container and said tubular member in said zone of taper, and thereby fracture said container as said cap is moved from its said first position to its said second position.

16. Apparatus as recited in claim 15 wherein:
said sealed container carries a first component of said biological testing system; and
a second component of said biological testing system is disposed within said tubular member,
whereby upon the fracturing of said sealed container, said first and second components of said biological testing system contact one another.

17. Apparatus for use in a liquid applicator comprising:
a substantially rigid tubular member having a zone of reduced interior cross section along its longitudinal axis and adapted to receive therein a sealed, frangible container carrying liquid to be applied by said applicator;
container support means transversely disposed within said tubular member and constructed to permit the flow of liquid therethrough;
applicator means disposed at the end of said tubular member opposite the end into which said container is introduced; and
flexible means insertable into said tubular member for wedgedly engaging said frangible container adjacent said zone of reduced cross section of said tubular member with sufficient force to rupture said container.

18. Apparatus for use in a liquid discharging apparatus comprising:
a substantially rigid tubular member having a zone of reduced interior cross section along its longitudinal axis and adapted to receive therein a sealed, frangible container carrying liquid to be discharged;
container support means transversely disposed within said tubular member and constructed to permit the flow of liquid therethrough;
discharge means disposed at the end of said tubular member opposite the end into which said container is introduced; and
flexible means insertable into said tubular member for wedgedly engaging said frangible container adjacent said zone of reduced cross section of said tubular member with sufficient force to rupture said container.

* * * * *